(12) United States Patent
Chevalier

(10) Patent No.: US 11,304,819 B2
(45) Date of Patent: Apr. 19, 2022

(54) INTERVERTEBRAL FUSION REMOTE MONITORING DEVICE

(71) Applicant: CLARIANCE, Beaurains (FR)

(72) Inventor: Eric Chevalier, Arras (FR)

(73) Assignee: CLARIANCE, Beaurains (FR)

( * ) Notice: Subject to any disclaimer, the term of this patent is extended or adjusted under 35 U.S.C. 154(b) by 0 days.

(21) Appl. No.: 16/427,839

(22) Filed: May 31, 2019

(65) Prior Publication Data
US 2020/0375756 A1 Dec. 3, 2020

(51) Int. Cl.
| | | |
|---|---|---|
| *A61F 2/44* | (2006.01) | |
| *A61F 2/46* | (2006.01) | |
| *A61B 5/00* | (2006.01) | |
| *A61B 5/11* | (2006.01) | |
| *A61B 17/00* | (2006.01) | |
| *A61F 2/48* | (2006.01) | |

(52) U.S. Cl.
CPC .......... *A61F 2/4455* (2013.01); *A61B 5/1126* (2013.01); *A61B 5/4851* (2013.01); *A61B 5/686* (2013.01); *A61F 2/4657* (2013.01); *A61B 5/0031* (2013.01); *A61B 2017/0011* (2013.01); *A61B 2562/0219* (2013.01); *A61F 2/488* (2021.08); *A61F 2002/4671* (2013.01)

(58) Field of Classification Search
CPC .......................... A61F 2/44–447; A61F 2/4611
See application file for complete search history.

(56) References Cited

U.S. PATENT DOCUMENTS

| | | | | |
|---|---|---|---|---|
| 9,820,869 | B2 * | 11/2017 | Aryan | A61F 2/4611 |
| 2005/0273170 | A1 * | 12/2005 | Navarro | A61F 2/442 623/17.13 |
| 2006/0247773 | A1 * | 11/2006 | Stamp | A61B 5/11 623/17.11 |
| 2009/0024161 | A1 * | 1/2009 | Bonutti | A61B 17/7225 606/213 |
| 2011/0044567 | A1 * | 2/2011 | Barbaroux | B01F 15/0085 383/120 |
| 2011/0295159 | A1 * | 12/2011 | Shachar | A61B 5/45 600/594 |
| 2013/0076157 | A1 * | 3/2013 | Stein | A61B 5/4566 307/116 |

(Continued)

*Primary Examiner* — Eduardo C Robert
*Assistant Examiner* — Steven J Cotroneo
(74) *Attorney, Agent, or Firm* — Nixon & Vanderhye

(57) ABSTRACT

Disclosed is an invasive intervertebral fusion cage, the intervertebral fusion cage including: a vibration sensor; and a frame configured to support surrounding tissues used to create a bone fusion process; wherein the vibration sensor is integral with the frame in order to measure the mechanical vibrations the vibrations arising from the medium consisting of the frame, the surrounding tissues and/or the fusionned bone, and wherein the intervertebral fusion cage does not include a vibration excitation transducer. Also disclosed is a remote medical monitoring device including a receiver for receiving data from an intervertebral fusion cage, reflecting the mechanical vibrations of a medium and a calculator computing from the received data a medium indicator by: determining at least one vibration pattern of the received data; comparing the at least one vibration pattern with at least one reference model; generating a medium indicator in function of the comparing step.

6 Claims, 5 Drawing Sheets

(56) References Cited

U.S. PATENT DOCUMENTS

| | | | |
|---|---|---|---|
| 2013/0079793 A1* | 3/2013 | Stein | A61F 2/4657 606/102 |
| 2013/0307955 A1* | 11/2013 | Deitz | A61B 5/746 348/77 |
| 2017/0135706 A1* | 5/2017 | Frey | A61B 17/1671 |
| 2017/0196508 A1* | 7/2017 | Hunter | A61B 17/70 |
| 2017/0231559 A1* | 8/2017 | Cuevas | A61B 5/14542 600/301 |

\* cited by examiner

INTERVERTEBRAL FUSION REMOTE MONITORING DEVICE

FIELD OF INVENTION

The present invention pertains to the field of the intervertebral fusion cage. In particular, the invention relates to a medical device comprising an intervertebral fusion cage.

BACKGROUND OF INVENTION

Spine fusion is the most common process in spine surgery treating numerous morbidities. It consists of two or more of the vertebrae that make up the spinal column fused together with bone grafts and internal devices that heal into a single solid bone. Spinal fusion can eliminate unnatural motion between the vertebrae and, in turn, reduce pressure on nerve endings. In addition, spinal fusion can be used to, for example, injuries to spinal vertebrae caused by trauma, protrusion and degeneration of the cushioning disc between vertebrae (sometimes called slipped disc or herniated disc), abnormal curvatures (such as scoliosis or kyphosis) and weak or unstable spine caused by infection or tumors.

Subjects who suffer degenerative disc disease, natural spine deformations, herniated discs, spine injuries or other disorders may require surgery on the affected region to relieve the individual from pain and prevent further injury to the spine and nerves. Spinal surgery may involve removal of damaged joint tissue, insertion of a tissue implant and/or fixation of two or more adjacent vertebral bodies. In some instances, a medical implant is also inserted, such as interbody cage.

If the bones are not weld together properly, then motion may continue across the area. For some patients, motion in that case can cause pain similar to that of a broken bone that never heals. When needed, x-rays and CT scans of the spine may be used to determine if a spinal fusion has occurred.

Unfortunately, these procedures can lead to failed solid bone fusion, or pseudarthrosis, which is a well-known iatrogenic complication. For patients with clinically suspected pseudarthrosis, several imaging modalities can be used. The most common radiographic findings suggestive of pseudarthrosis are implant failure or loss of fixation, radiolucency, and deformity. Plain radiography and CT scanning are the most common imaging modalities used to diagnose lumbar pseudarthrosis. However, CT scanning has significant limitations such as cost and radiation exposure. Furthermore, some spinal cage are non-well observable by radiography, especially which made of porous titanium.

Providing a monitoring system which can continuously or semi-continuously monitor and identify intervertebral bone architecture and bone fusion between adjacent vertebrae could provide welcome increase in spine fusion clinical outcome and better patient management by an in-vivo diagnosis of potential pseudarthrosis after surgery.

Therefore, the present invention is intended to provide an intervertebral fusion cage and a medical monitoring device to continuously or semi-continuously monitor and identify intervertebral bone architecture and bone fusion between adjacent vertebrae.

SUMMARY

The present invention relates to an invasive intervertebral fusion cage, said intervertebral fusion cage comprising:
a) a vibration sensor; and
b) a frame configured to support surrounding tissues used to create a bone fusion process;
wherein the vibration sensor is arranged within the frame, on the frame or is integral with the frame in order to measure mechanical vibrations, said vibrations arising from the medium consisting of the frame itself, the surrounding tissues and/or the fusionned bone, and wherein the intervertebral fusion cage does not comprise a vibration excitation transducer.

An advantage of the cage of the invention is that it can measure at least one parameter, preferably a range of parameters of the bone fusion process in order to give an indicator to an operator or a doctor, and the at least one parameter is a signature resulting from the vibration of the cage, the surrounding tissues, the physical integrity of the cage or the risk of failure and/or of the progress of the fusion representative of the state of the fusion. Thus, the arrangement of the sensor contributes to generate a relevant indicator.

In one embodiment, the intervertebral fusion cage comprises a computer-readable data carrier storing data acquired by the vibration sensor; and a wireless interface for transmitting said stored data to an external device.

In one embodiment, the intervertebral fusion cage is configured to be placed in an initial position between two vertebrae (L1, L2).

In one embodiment, the intervertebral fusion cage comprises at least one or at least two hollow or empty hole arranged to allow bone fusion process between the two vertebrae.

In one embodiment, the intervertebral fusion cage comprises an accelerometer.

In one embodiment, the at least one sensor of the cage is an accelerometer. In one embodiment, the cage of the invention encompasses only one sensor.

In one embodiment, the intervertebral fusion cage comprises at least one support element to control the space between the two vertebrae.

In one embodiment, the intervertebral fusion cage means for amplifying and/or filtering specific vibration frequencies to improve signal-noise-ratio.

According to a second aspect, the present invention further relates to a medical monitoring device comprising:
a) a receiver for receiving data from an intervertebral fusion cage, reflecting the mechanical vibrations of a medium consisting of the frame, the surrounding tissues (20) and/or the fusionned bone; and
b) a calculator computing from the received data a medium indicator (MI) by:
   i. determining at least one vibration pattern (VP) of said received data;
   ii. comparing said at least one vibration pattern (VP) with at least one reference model;
   iii. generating a medium indicator (MI), preferably selected from:
      a data related to the progress of the bone fusion process and/or;
      a density of a bone and/or;
      a thickness of a bone layer and/or;
      a stiffness of a bone layer and/or;
      a stiffness of the intervertebral fusion cage, said stiffness allowing deducing a physical integrity information of said cage.

In one embodiment, the calculator generates an indicator which preventively identifies the risk of failure.

In one embodiment, the calculator generates an offset indicator of the migration of the intervertebral fusion cage.

An advantage is to measure a criterion of the bone fusion process in order to give an indicator to an operator or a doctor which is representative of the state of the fusion. The processing steps of the signal contributes to generate a relevant indicator, for example by determining a relevant pattern and achieving correlation functions with some relevant values and for instance by comparing the different values of said pattern in a predefined duration.

In one embodiment, the monitoring device comprises a computer-readable data carrier storing data acquired by the receiver.

In one embodiment, the reference model comprises at least one reference vibration patterns. In one embodiment, said at least one reference vibration pattern includes an intervertebral fusion cage propagation model (temporal propagation); and/or at least a vibration pattern previously determined.

According to a third aspect, the present invention further relates to a medical system comprising an intervertebral fusion cage as described above and a medical monitoring device as described above, and the system comprises an interface which activates the transmission of vibration data measured into the intervertebral fusion cage in order to be received by the medical monitoring device.

According to a fourth aspect, the present invention further relates to a monitoring method for assessing the position or the physical integrity of an intervertebral cage or monitoring a bone fusion comprising: receiving data from an intervertebral fusion cage, comprising a vibration sensor; and a frame used to create a bone fusion process; wherein the vibration sensor is arranged within the frame in order to measure mechanical vibrations, said vibrations arising from the medium consisting of the frame, the surrounding tissues and/or the fusionned bone, and preferably the intervertebral fusion cage does not comprise a vibration excitation transducer; computing from the received data a medium indicator (MI) by determining at least one vibration pattern (VP) of said received data; comparing said at least one vibration pattern (VP) with a reference model; generating a medium indicator (MI) in function of the comparing step; displaying the medium indicator. The vibration pattern (VP) is also referred to as a signature of a patient's situation with regard to the interverbal stage and the bone fusion process.

Definitions

In the present invention, the following terms have the following meanings:

"Resonant frequency": refers to the frequency at which the response amplitude is a relative maximum.

"Bone grafting material" refers to a natural or synthetic or composite material which is able to serve as a scaffold for new bone growth that is perpetuated by the native bone, especially in order to improve the osteogenesis. In one embodiment, the cage of the invention is made of bone grafting material.

"Frame": means scaffold.

"Peak": refers to a frequency or a narrow range of frequency for which the response amplitude is a relative maximum.

"Physical integrity" refers to the mechanical structure of an object and to the fact that it remains unchanged overtime.

Assessing the "progress of bone fusion process": includes, not limitatively, evaluating bone quality, measuring bone stiffness, and/or assessing the presence of a bony bridge (i.e. a solid link made of bone material) at the location where the fusion is expected.

"Migration": refers to the displacement of an implant from its initial position.

"Vibration response" refers to amplitude of the motion of an object or a system on its own until it returns to its resting state.

"Young's modulus": refers to the elastic modulus, measuring the stiffness of a solid material.

"Vibration pattern", refers to a characteristic of a vibration data, said vibration pattern may be extracted from the measured vibration signal or from the vibration spectrum, or from another any resulting signals extracted from the vibration signal.

DETAILED DESCRIPTION

The following detailed description will be better understood when read in conjunction with the drawings. For illustrating, the medical device is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

According to a first aspect, the present invention, as illustrated on FIG. 1 relates to intervertebral fusion cage 10 comprising: a vibration sensor 11 and a frame 13 comprising at least two sides configured to support surrounding tissues used to create a bone fusion process.

The vibration sensor 11 is arranged between the two sides of the frame 13 in order to measure the mechanical vibrations of a medium, said medium being created by the frame, the surrounding tissues 20 and/or the fusionned bone.

The intervertebral fusion cage 10 comprises at least one vibration sensor 11 configured to measure a vibration response of medium. According to one embodiment, the intervertebral fusion cage 10 further comprises means for transmitting said measurements from the intervertebral fusion cage to the computer-readable data carrier.

According to one embodiment, the intervertebral fusion cage 10 further comprises a computer-readable data carrier storing data acquired by the vibration sensor and a wireless interface for transmitting said stored data to an external device.

According to one embodiment illustrated FIG. 2, the intervertebral fusion cage 10 is configured to be placed in an initial position between two vertebras L1, L2.

According to one embodiment, said intervertebral fusion cage 10 comprises at least one support element to control the space between the two vertebrae L1 and L2. According to one embodiment, said support element is included in the frame 13. A support element can be at least one tray or ridge or plane surface, optionally including spaces in between the at least one tray, ridge, endplate or plane surface or holes within said at least one tray, ridge or plane surface. According to one embodiment, the vibration sensor is arranged on the external surface of the frame 13. According to one embodiment, the vibration sensor 11 is integral with the frame 13.

The advantage of the intervertebral fusion cage 10 according to the present invention is to allow the monitoring of mechanical vibrations of the medium in order to give some information on the bone fusion process operating in said medium.

In one embodiment, the frame 13 of the intervertebral fusion cage 10 is made of metal, graphite, or bone, preferably made of titanium or polyether ether ketone (PEEK). According to one embodiment, the frame 13 of the intervertebral fusion cage 10 is made of porous titanium. According to one embodiment, the frame 13 of the intervertebral fusion cage 10 is made by 3D-printing. Preferably, the intervertebral cage 10 is cylinder in shape or rectangular in shape. In the following description, the term "implant" can also be used to refer to the intervertebral fusion cage 10.

As illustrated on FIG. 2, the intervertebral fusion cage 10 is configured to hold the two vertebrae (L1 and L2) apart while the fusion becomes solid. As illustrated on FIG. 3, the intervertebral fusion cage 10 is configured to be placed between two vertebrae (L1 and L2) and to be surrounded internally and/or externally with surrounding tissues 20.

According to one embodiment, the surrounding tissues 20 comprises the native biological tissues in contact or in the vicinity of the intervertebral cage. According to one embodiment, the surrounding tissues 20 further comprise the two vertebrae (L1, L2) on both side of the intervertebral cage 10.

According to one embodiment, said surrounding tissues 20 comprise bone grafting material placed in the vicinity of the vertebrae. According to one embodiment, said surrounding tissues 20 are bone grafting material. Bone grafting material aims at enhancing the bone fusion process between the two adjacent vertebrae. The bone grafting material used may be any bone grafting material used by one skilled in the art.

The bone grafting material may be a powder which will progressively merge to become stiffer and hardener. In one embodiment, the bone grafting material is bone powder or hydroxyapatite. According to another embodiment, a bony bridge of bone fusion can be achieved without any bone grafting material.

According to one embodiment illustrated on FIG. 4, the intervertebral cage 10 comprises a hollow center or an empty hole 12. According to one embodiment illustrated on FIG. 1, the intervertebral cage 10 comprises at least two hollow or empty holes 12 configured to allow the bone fusion between the two vertebrae L1, L2 through the hollow of the intervertebral fusion cage 10.

In one embodiment, the intervertebral fusion cage 10 is configured to be screwed to the superior and the inferior vertebrae between which it is configured to be placed. In one embodiment, the intervertebral fusion cage 10 comprises at least one screw thread. In one embodiment, the intervertebral fusion cage 10 may further comprise at least one fixation plate. The intervertebral fusion cage 10 may be attached to said plate with a screw or connected through a ball joint keeping the tilting movement of the intervertebral fusion cage 10 free.

According to one embodiment, the frame 13 of the intervertebral cage 10 is expandable. In this embodiment, the cage includes support elements that can be faces or ridges or trays. The expandable frame is positioned within the vertebral body and the faces or ridges or trays follow an expansion plane that corresponds to the desired bone recovery.

According to one embodiment, said intervertebral cage includes mechanical structures dedicated to filter specific vibration frequencies to improve signal-noise-ratio.

According to one embodiment, said intervertebral fusion cage comprises means for amplifying and/or filtering specific vibration frequencies to improve signal-noise-ratio.

The intervertebral fusion cage 10 further comprises at least one vibration sensor 11. The at least one vibration sensor is configured to measure a vibration response of a medium comprising said intervertebral fusion cage 10, said surrounding tissues 20 and/or the fusionned bone. According to one embodiment, the at least one vibration sensor is configured to measure a vibration frequency value and a vibration response value (i.e. amplitude) of said surrounding tissues 20.

According to one embodiment, the at least one vibration sensor 11 is on the cage.

According to one embodiment, the at least one vibration sensor 11 is in contact with surrounding tissues 20.

According to one embodiment, the at least one vibration sensor 11 is placed on the horizontal side of the intervertebral fusion cage 10. By horizontal side of the intervertebral fusion cage, it should be understood the surface which is directed to the adjacent vertebral endplate.

According to one preferred embodiment, the at least one vibration sensor 11 is a piezoelectric element. The piezoelectric vibration sensor, when exposed to a mechanical stress or a deformation, is able to provide an electric field. The current provided by the piezoelectric element is function of the intensity of the deformation (or stress). A piezoelectric element is so able to measure the amplitude and the frequency of the vibrations.

According to one embodiment, the cage further includes at least one sensor actuator configured to improve bone regeneration and/or bone fusion process.

In one embodiment, the vibration sensor is a piezoelectric element and said piezoelectric element, when activated, emits mechanical or ultrasound waves when activated. Said mechanical or ultrasound wave allow improving the bone regeneration.

In one embodiment, the sensor actuator enables the activation of said piezoelectric element.

In one embodiment, said waves are generated upon reception of information received by the vibration sensor. In one embodiment, said actuator is controlled by an external device. In one embodiment, the actuator activates the sensor according to a closed or open loop.

In one embodiment, the sensor actuator is driven by the mechanical vibrations of the medium or by the measured vibration response.

In one embodiment, the measured vibration response allows the control or the activation of the at least one sensor actuator according to a closed or opened loop system.

In one embodiment the sensor information allows the control of at least one actuator according to a closed or open loop system.

In general, vertebrae are exposed to a multitude of vibration during patient movements. Statistically, during a sufficiently long period of time, the system comprising the medium and the intervertebral fusion cage will be exposed to a large spectrum of frequencies.

The at least one vibration sensor 11 is configured to measure a vibration response value of said system comprising the intervertebral fusion cage 10 and said surrounding tissues 20. Indeed, the vibration sensor 11 is able to create an electric charge in response to applied mechanical stress. When a vibration occurs, said vibration sensor 11 measures the vibration response of said medium.

According to one embodiment, the at least one vibration sensor is configured to measure a vibration response of said system at a frequency ranging of from 20 Hz to 10000 Hz, preferably from 30 Hz to 7000 Hz, more preferably from 40 Hz to 5000 Hz.

According to one embodiment, the at least one vibration sensor is configured to measure a vibration frequency of said intervertebral fusion cage at a frequency ranging of from 20 Hz to 10000 Hz, preferably from 30 Hz to 7000 Hz, more preferably from 40 Hz to 5000 Hz.

In one embodiment, the term "measure" as to be understood by transforming the mechanical stress in electric current. The measurement is provided by an impedance meter which can be in the implant 11 or in an external device. In one embodiment, the at least one vibration sensor comprises at least one piezoelectric element and means to measure current, voltage and/or impedance provided by the at least one piezoelectric element. The at least one piezoelectric element and said means to measure current, voltage and/or impedance provided by the at least one piezoelectric element are connected each other by wires or wireless.

According to one preferred embodiment, the at least one vibration sensor 11 is an accelerometer element. Said accelerometer is an electromechanical device that may measure both static (gravity) and dynamic (motion or vibration) accelerations.

When the patient moves, specific constraints apply on vertebrae: extension, flexion, compression, torsion, etc. From the state of no fusion to the state where the fusion is completed, i.e. where bony bridge between vertebrae is effective, constraint such as extension leads to different vibration patterns. The integration of an accelerometer into the said intervertebral fusion cage 10 provides useful vibration patterns by the measurement of the acceleration time response: with a 3-axis accelerometer, the signal from the horizontal, vertical and axial direction can be captured; with an only one or 2 axis designs, the said accelerometer orientation is then critical.

According to one embodiment, said accelerometer can provide patient position and movement information for rehabilitation postoperative process.

As illustrated on FIG. 10, an accelerometer embedded in a intervertebral fusion cage provides a graph of time history.

According to one embodiment, the signal generated by the at least one vibration sensor 11 allows obtaining a frequency spectrum. In one embodiment, the signal generated by the at least one vibration sensor 11 is transformed by a Fourier transform or a wavelet transform to obtain a frequency spectrum.

According to one embodiment, this invention includes means for calculating a modal damping factor (MDF). Advantageously, in this invention, the frequency spectrum is used to calculate a damping factor which is proportional to the width of the resonant peak about the peak's center frequency.

According to one embodiment, said intervertebral fusion cage does not comprise a vibration excitation transducer. According to one embodiment, the vibration sensor used in the present invention is able to emit a vibration.

According to a second aspect, the present invention relates to a medical monitoring device comprising a receiver for receiving data from an intervertebral cage 10, said data corresponding to mechanical vibration of a medium. In one embodiment, said medium includes the frame, the surrounding tissues 20 and/or the fusionned bone.

The medical monitoring device further comprises a calculator computing from said received data, or data calculating or computed therfrom, into a medium indicator MI.

In one embodiment, said calculator comprises instructions for determining or calculating at least one vibration pattern of the medium and for comparing said vibration pattern with a vibration pattern of reference or with a reference model. From said comparison, the calculator is able to determining or generating a medium indicator MI in function of the comparing step.

In one embodiment, numerical or analogical amplifiers or filters may be used in order to treat the vibration signals before extracting a vibration pattern. A correlation method, for instance using maximum likelihood criteria, may be applied with some predefined signals having some predefined patterns in order to extract some vibration patterns of the measured signal.

In one embodiment, said medium indicator MI is, non limitatively, an indicator of a variation of the intervertebral bone fusion process of said surrounding tissue. According to another embodiment, the medium indicator MI is also an indicator of the migration of the intervertebral fusion cage 10 and/or of the physical integrity the intervertebral fusion cage 10, and/or of the risk of failure of the cage.

In one embodiment, the medical monitoring device is able to analyze the measurement obtained by the implant 10 and to provide a feedback on the fusion process of said surrounding tissues, on the migration and/or on a physical integrity information of the implant 10. According to one embodiment, the medical monitoring device is comprised in an external device and is not configured to be implanted in a patient body. According to one embodiment, said external device is configured to be placed outside the body of the user. According to one embodiment, said external device is a belt, preferably an abdominal belt.

According to one embodiment, said external device further comprises an impedance meter, and/or a user interface such as a display. According to one embodiment, said user interface is required to allow the user to provide its measurement parameters and to inform him about the fusion process status or/and the implant migration and/or physical integrity of said implant, especially early information about the risk of failure of the implant.

By "physical integrity information", it should be understood any information on a modification or dysfunctionement in the mechanical structure of the implant. A modification of the mechanical structure of the implant may occur in case of, for example, a beginning of dislocation or of breakage, deformation or the propagation of a crack in the implant. Indeed, the implant is continuously subject to vibrations. According to one embodiment, the medical monitoring device of the invention is able to measure the young modulus of the implant and to deduce from said young modulus its physical integrity.

According to one embodiment, the external monitoring device of the invention comprises a memory unit able to store the measurements made by the at least one vibration sensor 11.

The present invention uses the measure of the vibration response to provide information on the implant and or the surrounding tissues 20.

After the implantation of the intervertebral fusion cage 10 on the user body, a process of bone fusion is expected between the two vertebrae L1 and L2. The variation of stiffness of surrounding tissues 20 is directly linked to the bone fusion process. In one embodiment, the bone fusion process is the percentage of fusion between the step of the implementation in the user body and the step wherein a bridge of bone (also referred to as bony bridge) is made between the two vertebrae.

Fusion process is generally approximated by a homogeneous increase of the material stiffness or Young's modulus and then, the variation of the vibration response can lead to the information of the fusion process status of the surrounding tissues 20. For example, the Young's modulus of the bone grafting material before bone fusion is about 50 MPa. The Young's modulus of the one grafting material when the fusion is complete is around 1000 MPa. According to one embodiment, surrounding tissues 20 can form a "bridge" of bone and the presence of such bridge involve a modification of the vibration pattern of the medium.

According to one embodiment, the medical monitoring device comprises a memory unit able to store information, to obtain, from the at least one vibration pattern, the stiffness of surrounding tissues 20 or of the bone grafting material or to obtain the Young's modulus of the bone grafting material. According to one embodiment, said memory unit is able to store information to obtain, from the at least one vibration pattern, a medium indicator.

Furthermore, a migration of the intervertebral fusion cage, when placed between two vertebrae can be monitored by monitoring said vibration pattern. An asymmetry in the system comprising the intervertebral fusion cage and the surrounding tissues 20 change the structure of this system and so, lead to a variation of the vibration pattern of said system.

The medical monitoring device of the invention can achieve, from the vibration pattern of said system, to get the user information of the migration of the implant around its initial position. According to one embodiment, the present invention is able to detect a migration of the implant of at least 0.5 mm, 1 mm, 2 mm, 3 mm or at least 4 mm.

According to one embodiment, a defect or a failure in the implant, such as a crack or a fissure, can be monitored by monitoring said vibration pattern. Detecting such defect or failure permits to anticipate a break of the cage.

Because of the movement of the human body during a day, the bone grafting material constituting the cage is continuously exposed to vibrations. These vibrations are associated to various frequencies. By recording continuously these frequencies with the at least one vibration sensor, the applicant found that, with enough time (from several hours to a few days), a wide range of frequencies were recorded which can allow the medical monitoring device to study the vibration response on a wide range of frequencies.

The measurement of said vibration leads to the observation of some vibration patterns.

In one embodiment, said vibration pattern is the resonant frequency. Generally, when a solid material is exposed to vibrations, the response of said material to said vibration is sensibly the same. However, there is a few specific frequencies for which the response is relevantly higher than at the other frequencies. These specific frequencies are called resonant frequencies.

According to another embodiment, several vibration patterns can be used to achieve a single purpose. As an example, such vibration pattern can be a feature of the frequency spectrum. As another example, such vibration pattern can also be the amplitude of the signal at one predetermined frequency or the measures spectrum of frequencies. In one embodiment, the vibration pattern includes an intervertebral fusion cage propagation pattern (temporal propagation).

In another embodiment, the vibration pattern is the vibration response measured at a predetermined number of frequencies. For example, the vibration pattern can be the vibration response of the system at sensibly 2000, 2500, 3000, 4000 and/or 4500 Hz. The vibration response at these frequencies should be compared with the vibration response of reference.

According to one embodiment, said vibration pattern is the amplitude of the signal at a predetermined frequency. According to one embodiment, said vibration pattern is a mathematical transform of the vibration response such as a Fourier transform or a wavelet transform. According to one embodiment, said vibration pattern is a variation of the frequency during the time.

According to the present invention, the calculator comprises at least one reference model. According to one embodiment, the medical monitoring device of the invention comprises a memory unit comprising at least one vibration model.

According to one embodiment, said vibration model comprises at least two vibration patterns of reference: a first vibration pattern of reference corresponding of the vibration pattern value when the fusion process has not been started (for example, at the time of the implantation), and a second vibration pattern of reference value corresponding to the vibration pattern value when said fusion process is complete.

According to one embodiment, the vibration model comprises at least one vibration pattern of reference corresponding to the position of the intervertebral fusion cage in its initial position. According to one embodiment, said vibration model can be stored manually or measured following to the implantation of the implant.

In one embodiment, the reference model comprises at least one reference vibration pattern. In one embodiment, said at least one reference vibration pattern includes an intervertebral fusion cage propagation model (temporal propagation); and/or at least a vibration pattern previously determined.

By "following to the implantation", it has to be understood here "a few minutes, a few hours or a few days after the implantation of the implant in the user body".

According to an embodiment, vibration pattern is a resonant frequency. In one embodiment, said at least one reference resonant frequency is measured by the at least one vibration sensor following the implantation of the implant.

From the measurement of the vibration response, a computer connected to the computer-readable data carrier is able to calculate the at least one vibration pattern of the system and any other suitable information from the recorded data.

According to one embodiment wherein the vibration pattern is the resonant frequency: the computer scans the vibration response measured for each vibration frequency of the measured spectrum of frequencies and determines at least one resonant frequency of reference for which the vibration response is relevantly higher than for the other frequencies. From said resonant frequency value, the monitoring medical device according to the present invention calculates the difference between said resonant frequency and the resonant frequency of reference. Then, the medical monitoring device is able, from said calculated difference, to deduce or calculate a variation of the intervertebral fusion of the surrounding tissues 20 or a migration of the intervertebral fusion cage and to compute this information into a displayable indicator.

In one embodiment, the calculator comprises instructions which, when executed, computes from the received data a medium indicator MI by:

i. determining at least one vibration pattern VP of said received data;

ii. comparing said at least one vibration pattern VP with a reference model;

iii. generating a medium indicator MI in function of the comparing step.

According to one embodiment wherein the vibration pattern is the resonant frequency of the medium, the calculator carries out the step of:

a) determining at least one resonant frequency value of said medium from the received data;

b) comparing said at least one resonant frequency value and the at least one reference model;

c) generating a medium indicator MI in function of the comparing step.

In one embodiment, the steps carried out by the calculator are iteratively carried out. In one embodiment, the steps carried out by the calculator are carried out in a closed loop method. In one embodiment, the calculator semi-continuously executes these steps to semi-continuously generate a medium indicator. In one embodiment, the calculator continuously executes these steps to continuously generate a medium indicator.

In one embodiment, the term "said received data", refers here to the vibration frequency values and the vibration response values measured by the at least one vibration sensor.

In one embodiment, the medical monitoring device comprises a memory to store the vibration response measured by the at least one vibration sensor during a predetermined time. According to one embodiment, the predetermined time is long enough to obtain data which enable the calculator to determine the at least one resonant frequency.

According to one embodiment, the received data is a spectrum of frequency. According to one embodiment, the predetermined time is at least 1 hour, 2, 3, 4, 5, 6, 7, 8, 9, 10, 11, 12, 16, 20, 24, 30, 36, 42, or at least 48 hours.

According to one embodiment, the received data is a spectrum of frequency.

According to one embodiment wherein the vibration pattern is the resonant frequency of said medium, the step of determining at least one resonant frequency value of said medium from the received data, comprises the following steps of:

from the received data; scanning for each frequency the vibration response of said system;

identifying one or more peak of said vibration response;

optionally recording the frequency value of the center of said at least one peak;

optionally labelling said frequency value as the vibration pattern.

As illustrated in FIG. 6, the medium can comprise two or at least two resonant frequencies F1 and F2, and these two resonant frequencies can be calculated by the medical monitoring device.

According to one embodiment, the calculator comprises at least two reference models, a first reference model to generate a medium indicator from F1 and a second reference model to generate a medium indicator from F2.

According to one embodiment, the reference model comprises at least one equation which follows the evolution of the at least one vibration pattern in function of the medium indicator MI.

According to one embodiment, the reference model comprises data from which the calculator can found the migration of the intervertebral fusion of said surrounding tissues 20 by the vibration pattern. FIGS. 7, 8, and 9 are each an example of reference model. The reference model can also be a database.

In one embodiment, the reference model comprises some predefined vibration patterns, for example defined in a predefined amplitude range, a predefined frequency range and a predefined phase range of the signal.

In one embodiment, the reference model comprises some predefined spectral density with different values associated to different patterns.

In one embodiment, the reference model comprises a repetition of likehood patterns in a predefined duration.

According to another embodiment, the computer-readable data carrier comprises a modeling of the values of the at least one resonant frequency in function of the variation of stiffness of the bone grafting material and the implant migration.

In some scenarios, one of these parameters (such as for example, non limitatively, implant migration or intervertebral fusion of the surrounding tissues and/or risks about the physical integrity) is known by the computer. For example, during approximatively one day after the implantation of the implant in the user body, the bone fusion process of the bone grafting material has not yet started. The calculated difference is therefore function of one parameter: the migration of the implant. According to one embodiment, the computer-readable data carrier is able to store said value of the migration implant. In one embodiment, the implant is screwed to the vertebrae and cannot migrate after the operation. In said embodiment, said migration of the implant is constant and the resonant frequency value is only function of the intervertebral fusion of the surrounding tissues.

According to one embodiment, the calculator generates an offset indicator of the intervertebral fusion cage in function of the step of comparing the at least one vibration pattern with a reference model. In one embodiment, the offset indicator corresponding to a migration of the intervertebral fusion cage around its initial position and preferably to a migration of the intervertebral fusion cage around its initial position along the x and/or y axis illustrated on FIG. 5.

According to one embodiment, the at least one reference model comprises a first reference model to generate a medium indicator and a second reference model to generate an offset indicator of the intervertebral fusion cage around its initial position.

According to one embodiment, among the two following indicators: the medium indicator and the offset indicator, one of said indicator is known and is used to calculate the other one.

According to one embodiment, reference model comprises:

a) at least reference vibration patterns; and/or b) an intervertebral fusion cage propagation model; and/or c) at least a vibration pattern previously determined.

According to one embodiment, said computer-readable data carrier further comprises instructions which, when executed by a computer, cause the computer to carry out the step of:

calculating the difference between said at least one resonant frequency value and the at least one reference resonant frequency when the implant is implanted such as there is no bone fusion;

from said calculated difference, calculating the migration of said intervertebral fusion cage.

According to one embodiment, the medical device further comprises a memory unit.

Preferably, said memory unit is comprised in the external device. Said memory unit is connected to the calculator.

According to one embodiment, said medium indicator MI comprises:

a) a data related to the progress of the bone fusion process and/or;
b) a density of a bone and/or;
c) a thickness of a bone layer and/or;
d) a stiffness of a bone layer and/or;
e) a stiffness of the intervertebral fusion cage, said stiffness allowing deducing a physical integrity information of said cage.

According to one embodiment, said medical monitoring device further comprises a display and display is configured to display at least the medium indicator MI.

In one embodiment, the bone layer has to be understood as the layer between the two vertebrae of bone or of bone grafting materiel. Said bone layer may be the layer wherein the bone fusion process occurs or will occur.

According to one embodiment, the medical device further comprises an alarm. Said alarm can be a visual or an audible alarm. Said alarm may be activated by a value of said medium indicator or by a value of the offset indicator is one of said value exceed a predetermined threshold.

According to one embodiment, the step of comparing at least one vibration pattern (VP) with at least one reference model comprising the step of: calculating the difference the at least one vibration pattern value and the reference model value and comparing said difference to a predetermined threshold. According to one embodiment, said predetermined threshold is ranging from 1% to 7% of the reference model value, preferably ranging from 0.5% to 10% or ranging from 0.5% to 20%.

According to one embodiment, the intervertebral fusion cage 10 and the medical monitoring device both participates to achieve the same objective which is providing a monitoring system which can continuously or semi-continuously monitor and identify intervertebral bone architecture and bone fusion between adjacent vertebrae.

A third aspect of the present invention relates to a method for generating a medium indicator comprising:
a) a receiving data from an intervertebral fusion cage, corresponding to mechanical vibrations of a medium
b) computing from the received data a medium indicator MI by:
  i. determining at least one vibration pattern VP of said received data;
  ii. comparing said at least one vibration pattern VP with a reference model;
  iii. generating a medium indicator MI in function of the comparing step.

According to one embodiment, said method or the step b) further comprises the step of: generating an offset indicator of the intervertebral fusion cage in function of the comparing step.

According to one embodiment, the method of the invention includes calculating a modal damping factor (MDF). Advantageously, in this invention, the frequency spectrum is used to calculate a damping factor which is proportional to the width of the resonant peak about the peak's center frequency. This embodiment can be of particular advantage, as the damping factor detected with a vibration method may provide additional information on bone fusion process.

In one embodiment, said method further comprises the step of producing an alert signal in function of the comparing step, optionally if said comparison exceed a predetermined threshold.

In one embodiment, said method is a closed loop method. In one embodiment, the present method comprises iteratively the steps a) and b). In one embodiment, the method semi-continuously executes these steps to semi-continuously generate a medium indicator. In one embodiment, the method continuously executes these steps to continuously generate a medium indicator.

In one embodiment, the sensor actuator is driven by the medium indicator or by the vibration pattern of the received data.

In one embodiment, the medium indicator allows the control or the activation of the at least one sensor actuator according to a closed or opened loop system. In one embodiment, said system comprises the monitoring device and the intervertebral fusion cage.

In one embodiment, said method comprises the step of actuating the sensor actuator to emit mechanical or ultrasound waves, optionally in the direction of the empty hole, improving the bone regeneration or the bone fusion process.

According to one embodiment, said alert signal is produced by an alarm. Said alert signal can be a visual alert on the display, an audible alert, or an alert on an alert on an external device such a smartphone which is connected to the medical device.

According to a first example, said alert signal is an acoustic alarm emitted by a loudspeaker. In a second example, the alert signal is a visual alert represented on the display of the medical device. In a third example, the alert signal is a message in the form of an e-mail or a notification sent to the medical staff.

In one embodiment, the determination of at least one vibration pattern VP of said received data comprises a computation of the acceleration time response.

In one embodiment, the step of determining at least one vibration pattern further comprises the steps of:
  i. identifying a carrier frequency by applying a time-frequency transformation to the received data;
  ii. applying a narrow band pass filter at the carrier frequency to generate a filtered signal;
  iii. optionally, applying a noise filter in order to filter undesired frequencies;
  iv. extracting an envelope of the filtered signal to create an extracted signal; and
  v. applying time and frequency analysis to the extracted signal.

In a fourth aspect, the present invention further relates to a medical monitoring system device comprising an intervertebral fusion cage 10 according to the first aspect of the present invention and a medical monitoring device according to the second aspect of the present invention, wherein it comprises an interface which activates the transmission of vibration data measured into the intervertebral fusion cage in order to be received by the medical monitoring device.

In one embodiment, the medical monitoring system is configured to execute the method according to the third aspect of the present invention.

In one embodiment, the receiver of the medical monitoring device comprises at least one receiver. In one embodiment, the medical monitoring device further comprises means for ensuring a bi-directional communication between the user interface and the intervertebral fusion cage 10, or between the medical monitoring device and the intervertebral fusion cage 10, or between the calculator and the vibration sensor 11.

According to one embodiment, the medical monitoring device comprises means for transmitting and receiving data to the intervertebral fusion cage. According to a completer embodiment, the intervertebral fusion cage medical monitoring device comprises means for transmitting and receiving data to the medical monitoring device.

According to one embodiment, said medical monitoring device comprises a receiver. In one example, this receiver may be arranged in the vicinity of the body of a patient having such invasive intervertebral fusion cage. In one example, this receiver may be attached to a belt or any other portable equipment. In one example, the receiver is placed on the back of the user body, at the level of the implanted intervertebral fusion cage 10. One advantage of ensuring a proximity between the receiver and the invasive intervertebral fusion cage is to improve the quality of transmissions. In one embodiment, the receiver may be included in a smartphone having one dedicated software configured to treat the received data. The wireless interface may be supported by a Bluetooth interface.

According to one embodiment, the medical monitoring device comprises means for providing energy. According to one embodiment, the medical monitoring device provides the energy to the intervertebral fusion cage 10. According to one embodiment, the medical monitoring device comprises wireless power transferring means supplying energy to the intervertebral fusion cage 10. According to one embodiment, the medical monitoring device comprises a wireless transmitter connected to a power source.

According to one embodiment, the intervertebral fusion cage 10 comprises at least one receiver. According to another embodiment, the intervertebral fusion cage 10 comprises a receiver connected with wire to the vibration sensor 11. According to one example, the wireless transmitter connected to a power source conveys the field energy across an intervening space to said receiver. In this example, the receiver converts back the field energy to an electrical current.

In said embodiment, the medical monitoring device is able to provide energy to the means for transmitting data.

In one preferred embodiment, the intervertebral fusion cage 10 comprises at least a receiver for receiving energy and at least one transmitter for transmitting the measurements to the external device.

In a fifth aspect, the present invention relates to a medical monitoring system comprising an intervertebral fusion cage 10 and a computer-readable data carrier, said intervertebral fusion cage 10 being configured:
- to be placed in an initial position between two vertebras L1, L2; and
- to be surrounded internally and/or externally with surrounding tissues 20.

According to this aspect, the intervertebral fusion cage 10 comprises at least one vibration sensor 11 configured to measure a vibration response of a medium, said medium being created by the frame, the surrounding tissues and the fusionned bone.

Said medical monitoring system further comprises means for transmitting said measurements from the intervertebral fusion cage 10 to the computer-readable data carrier.

According to one example, the computer-readable data carrier comprises at least one vibration pattern of reference and instructions which, when executed by a computer, cause the computer to carry out the step of:
a) determining at least one vibration pattern of said system from the measured vibration response;
b) comparing said at least one vibration pattern and said vibration pattern of reference;
c) determining from said comparison, an intervertebral fusion of said surrounding tissues 20 and/or a migration of the intervertebral fusion cage 10, and/or the physical integrity information of the intervertebral fusion cage 10.

While various embodiments have been described and illustrated, the detailed description is not to be construed as being limited hereto. Various modifications can be made to the embodiments by those skilled in the art without departing from the true spirit and scope of the disclosure as defined by the claims.

REFERENCES

10—Intervertebral fusion cage
11—Vibration sensor
12—Empty hole of the intervertebral fusion cage
13—Frame
20—Surrounding tissues
L1—Vertebrae
L2—Vertebrae
F1—First resonant frequency
F2—Second resonant frequency

EXAMPLES

The present invention is further illustrated by the following examples.

In said example, the vibration pattern chosen was the resonant frequency.

Example 1: Measuring of the at Least One Resonant Frequencies

Materials and Methods
Material
An intervertebral fusion cage according to the present invention is implemented in a simulator simulating vibration. The simulator allows generating vibrations which can occurred between the human vertebrae. In this example, the intervertebral fusion cage is externally and internally surrounded by a bone grafting material.

According to one setup, the bone grafting material Young's modulus has been set to 1 GPa, which corresponds to a fusion bone completion.

The migration of the implant has been set to 0 mm.

Methods

During the simulation, the frequencies and the vibration responses were measured by the vibration sensor.

Results

Figure 6:
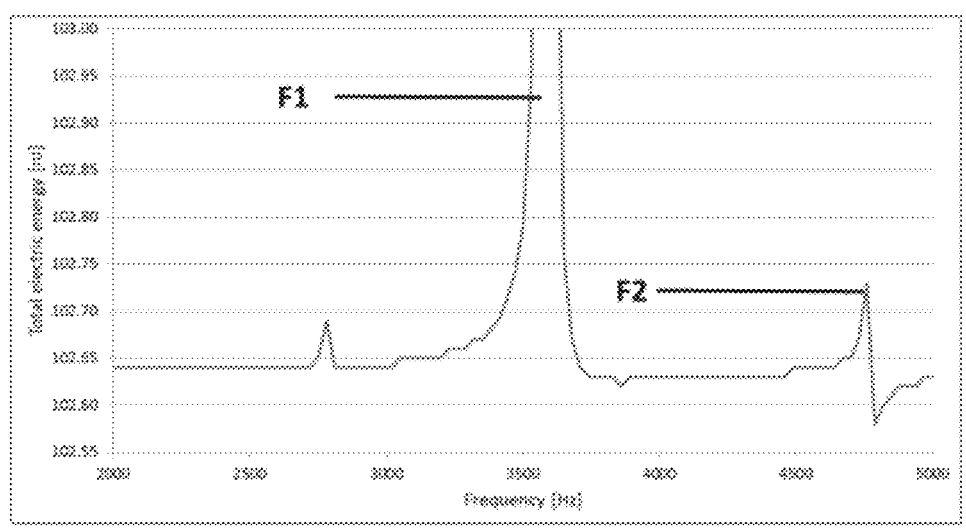
FIG. 6 is a graph of the vibration response measured by the vibration sensor in function of the frequency.

The vibration response measured is illustrated on FIG. 6. It can be seen that the vibration response of the bone grafting material is increased at two specific frequencies: around 4800 Hz (F2) and 3500 Hz (F1). For the other frequencies, the vibration response is sensibly the same for a spectrum of frequency from 2000 Hz to 5000 Hz.

The resonant frequencies are so 4800 Hz and 3500 Hz.

Example 2: Bone Fusion Process Impact on Resonant Frequencies

Materials and Methods

Material

A medical device according to the present invention was used in a simulator simulating vibration which can be caused between the human vertebrae.

Methods

The migration of the implant has been set to 0 mm.

The Young's modulus of the bone grafting material has been ranging from 50 MPa (no bone fusion) to 1000 MPa (fusion bone completion).

Results

Figure 7:
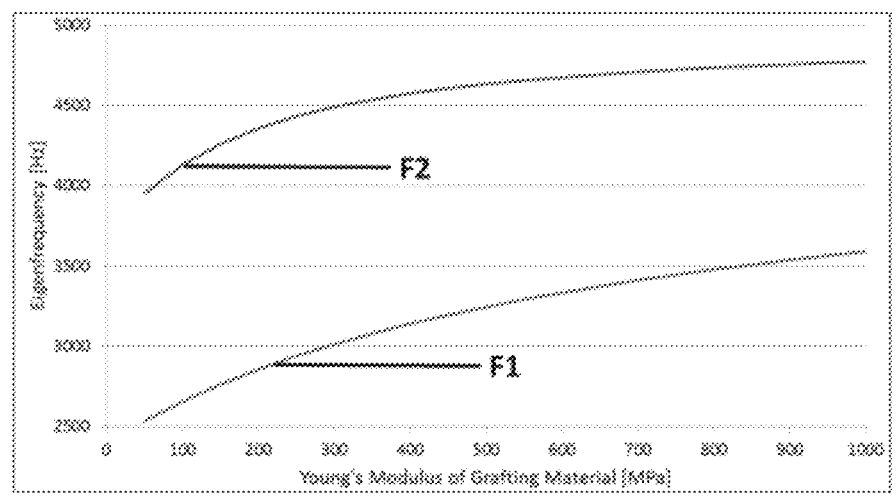
FIG. 7 is a graph of the frequency of the two resonant frequencies in function of the Young's Modulus of the bone grafting material.

The calculated resonant frequencies for each bone grafting material's Young's modulus are illustrated on FIG. 7. Both resonant frequencies increase with a progression of the fusion process. Both resonant frequencies could be considered for bone fusion monitoring.

Example 3: Cage Displacement Impact on Resonant Frequencies

Materials and Methods

Material

According to one example, a medical device according to the present invention is implemented in a simulator simulating vibrations. The vibrations generated are preferably in the same range of those caused between the human vertebrae.

Methods

The Young's modulus of the bone grafting material has been set to 50 MPa (no bone fusion).

Figure 1:
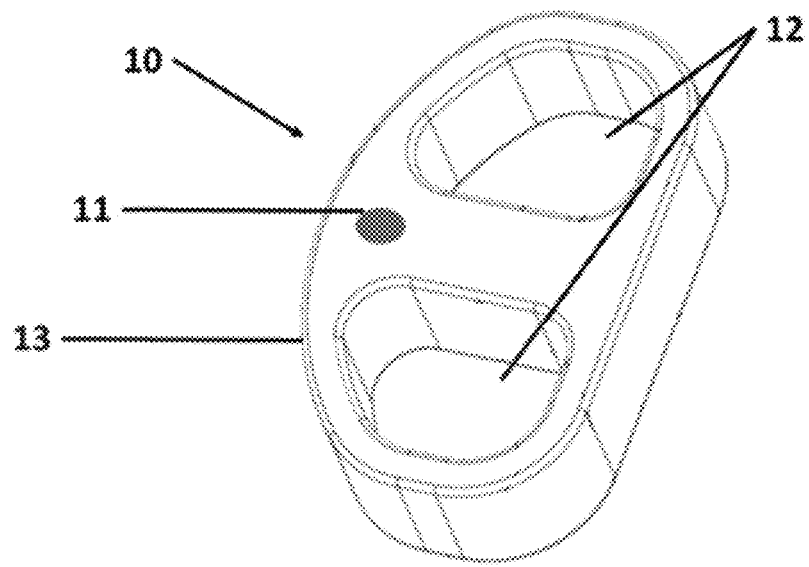
FIG. 1 is a drawing of the intervertebral fusion cage according to one embodiment of the present invention.
Figure 2:
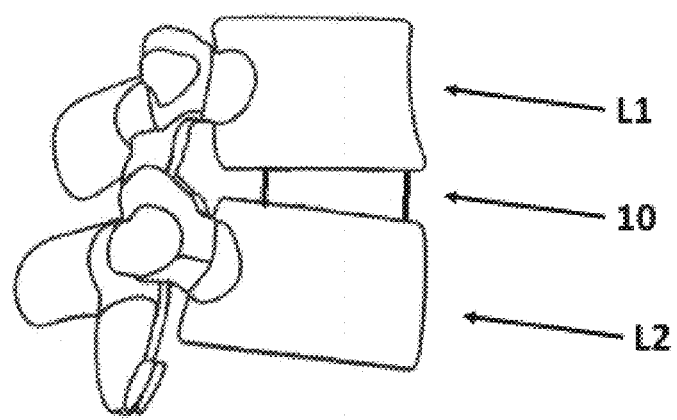
FIG. 2 is a drawing of the intervertebral fusion cage according to one embodiment between two vertebrae.
Figure 3:
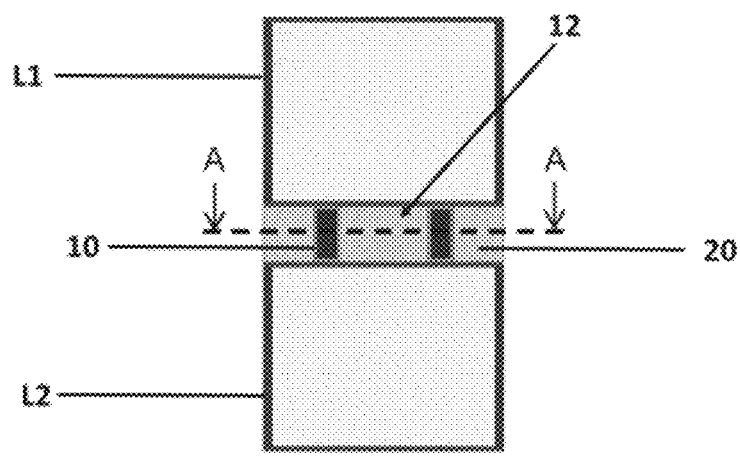
FIG. 3 is a cross-sectional view of the intervertebral fusion cage between two vertebrae and surrounded internally and externally by a bone grafting material according to one embodiment of the present invention.
Figure 4:
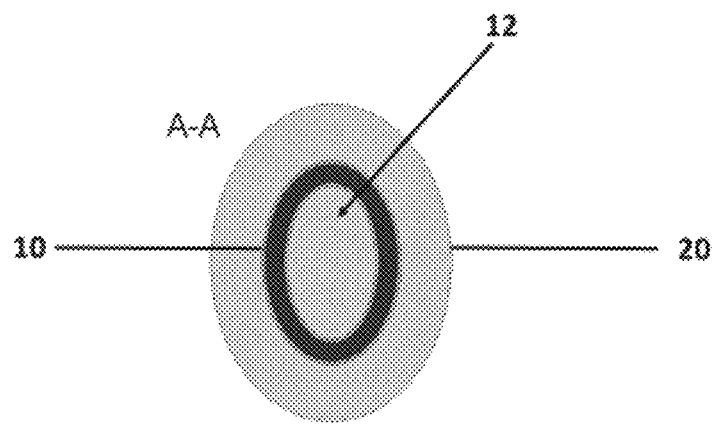
FIG. 4 is a cross-sectional view in the direction of the AA axis of the intervertebral fusion cage surrounded internally and externally by a bone grafting material.
Figure 5:
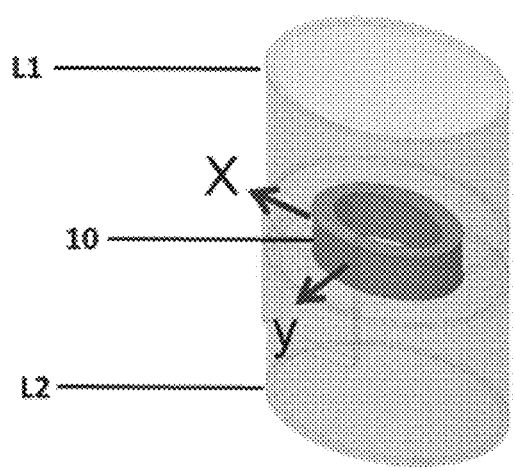
FIG. 5 is a drawing of the intervertebral fusion cage according to one embodiment of the present invention between two vertebrae.

The position of the implant has been moved from its initial position according to the x or they axis illustrated on FIG. 5.

Results

Figure 8:
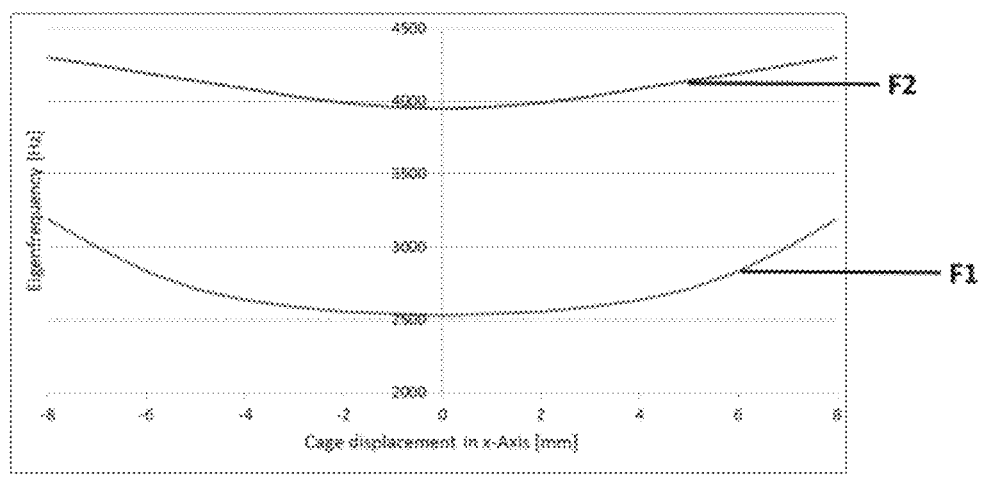
FIG. 8 is a graph of the frequency of two resonant frequencies in function of the intervertebral fusion cage migration along the x-axis of FIG. 5.
Figure 9:
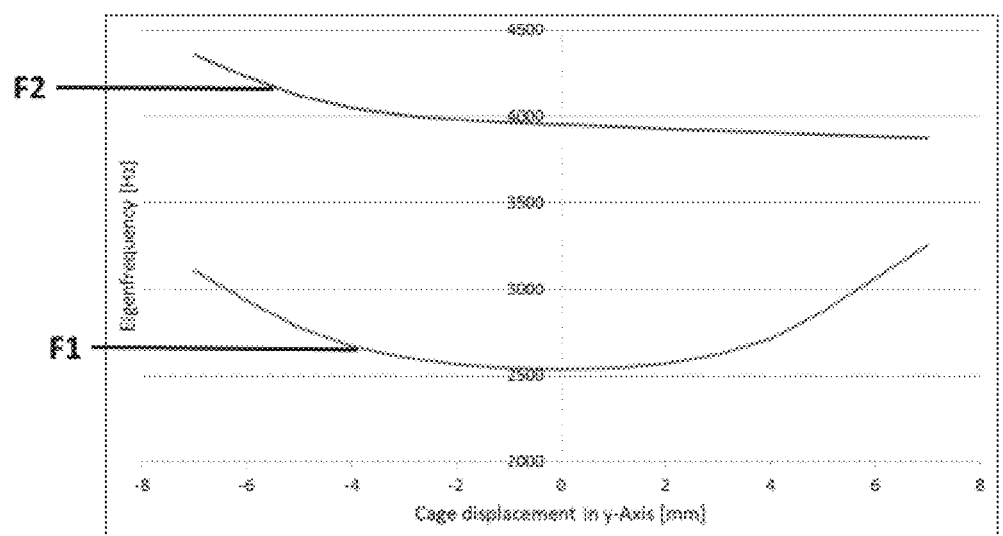
FIG. 9 is a graph of the frequency of two resonant frequencies in function of the intervertebral fusion cage migration along the y-axis of FIG. 5.
Figure 10:
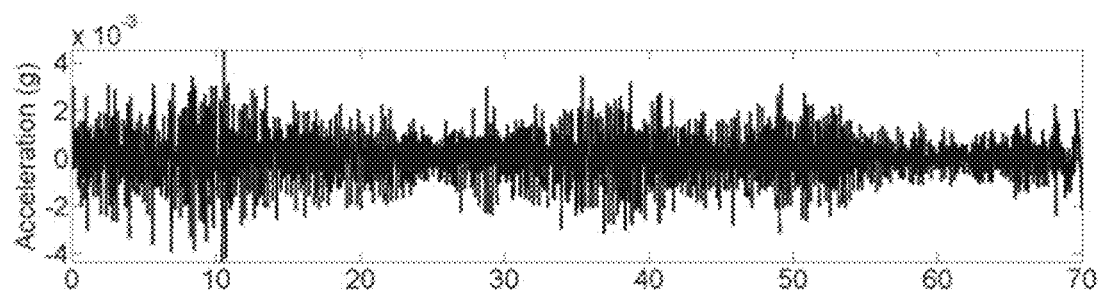
FIG. 10 is a graph of a time history from an accelerometer signal embedded in the intervertebral fusion cage.

The calculated resonant frequencies when the cage has been displaced along the x axis are illustrated on FIG. 8 and the calculated resonant frequencies when the cage has been displaced along the y axis are illustrated on FIG. 9.

Both resonant frequencies present a sensitivity to a displacement of the implant in the x or y direction. After their implantation into the user body, when there is still no bone fusion, the present invention allows checking the position of the intervertebral fusion cage and calculating the migration of said intervertebral fusion cage around its initial position.

As it can see on FIGS. 8 and 9, the bone grafting material comprises two resonant frequencies. Both resonant frequencies have not the same evolution when the migration of the implant is varying. The resonant frequency F2 cannot be used to monitor the migration of the implant.

By using the two resonant frequencies F1 and F2, the medical monitoring system is able to calculate at least two indicators. The first indicator corresponds to the Young's modulus of medium related to the progress of the bone fusion process. The second indicator corresponds to the offset indicator of the intervertebral fusion cage.

The invention claimed is:

1. An invasive intervertebral fusion cage (10), said intervertebral fusion cage (10) comprising:
    a frame (13), configured to support surrounding tissues (20) used to create a bone fusion process upon a bone;
    at least one vibration sensor (11) located in an interior of a structure of the frame (13);
    a non-transitory computer-readable data carrier storing data acquired by the vibration sensor;
    a wireless interface for transmitting said stored data to an external device; and
    a sensor actuator,
    wherein the vibration sensor (11) is integral with the frame (13) and measures mechanical vibrations arising from a medium consisting of one or more of the frame (13), the surrounding tissues (20), and the bone subject to the bone fusion process,
    wherein the intervertebral fusion cage does not comprise a vibration excitation transducer,
    wherein the intervertebral fusion cage is configured to be placed in an initial position between two vertebrae (L1, L2),
    wherein the vibration sensor, in an activated state, emits mechanical or ultrasound waves, and
    wherein the sensor actuator is configured to activate the vibration sensor,
    the vibration sensor emitting said mechanical or ultrasound waves when activated by said sensor actuator,
    and the vibration sensor and the sensor actuator together form a control loop wherein information from the vibration sensor of the measured mechanical vibrations controls said sensor actuator in order for said sensor actuator to activate the vibration sensor for emission of the mechanical or ultrasound waves.

2. The intervertebral fusion cage (10) according to claim 1, further comprising:
    at least two hollow or empty holes (12) arranged to allow the bone fusion process between the two vertebrae.

3. The intervertebral fusion cage (10) according to claim 1, further comprising:
    at least one support element configured to control a space between the two vertebrae.

4. The intervertebral fusion cage (10) according to claim 1, wherein said intervertebral fusion cage comprises only one sensor.

5. The intervertebral fusion cage (10) according to claim 1, wherein said intervertebral fusion cage comprises an accelerometer, or wherein the sensor is an accelerometer.

6. A medical system, comprising an intervertebral fusion cage (10) according to claim 1, and a medical monitoring device,
    wherein the medical monitoring device comprises:
    a receiver that receives data from the intervertebral fusion cage, the data received by the receiver reflecting mechanical vibrations of a medium consisting of one or more of the frame of the intervertebral fusion cage, surrounding tissues (20), and a bone to undergo a bone fusion process; and a calculator configured to compute, from the data received by the receiver, a medium indicator (MI) by:
  determining at least one vibration pattern (VP) of said received data;
  comparing said at least one vibration pattern (VP) with at least one reference model;
  generating the medium indicator (MI), which includes at least one of:
    a data related to the progress of the bone fusion process,
    a density of the bone,
    a thickness of a bone layer,
    a stiffness of the bone layer, and
    a stiffness of the intervertebral fusion cage, from which a physical integrity information of the intervertebral fusion cage is deduced;
wherein the medical system further comprises an interface which activates a transmission of vibration data measured into the intervertebral fusion cage in order to be received by the medical monitoring device.

* * * * *